United States Patent [19]

Mayeaux

[11] Patent Number: 4,842,709

[45] Date of Patent: Jun. 27, 1989

[54] ELECTROLYTIC CELL AND PROCESS FOR THE OPERATION OF ELECTROLYTIC CELLS, FOR MOISTURE ANALYZERS

[75] Inventor: Donald P. Mayeaux, Prairieville, La.

[73] Assignee: EG&G Chandler Engineering, Tulsa, Okla.

[21] Appl. No.: 129,602

[22] Filed: Dec. 7, 1987

[51] Int. Cl.⁴ ............................................. G01N 27/46
[52] U.S. Cl. ................................. 204/402; 204/1 T; 204/430; 73/335; 73/336.5
[58] Field of Search .............. 204/1 W, 430, 402, 400; 73/335, 336, 336.5

[56] References Cited

U.S. PATENT DOCUMENTS

| | | | |
|---|---|---|---|
| 3,073,772 | 1/1963 | Wirz et al. | 204/402 |
| 3,367,850 | 2/1968 | Johnson | 204/430 |
| 3,410,779 | 11/1968 | Whitehead et al. | 204/435 |
| 4,021,199 | 5/1977 | Mukae et al. | 204/402 |
| 4,050,995 | 9/1977 | Bredeweg | 204/430 |
| 4,447,309 | 5/1984 | Morioka et al. | 204/402 |
| 4,589,971 | 5/1986 | Mayeaux | 204/430 |
| 4,713,164 | 12/1987 | Krietemeier et al. | 204/400 |

FOREIGN PATENT DOCUMENTS

895210   5/1962   United Kingdom ................ 204/402

Primary Examiner—T. Tung
Attorney, Agent, or Firm—Llewellyn A. Proctor, Sr.

[57] ABSTRACT

An improved electrolytic cell, the electrodes of which can be readily cleaned, and resensitized by the application of fresh electrolyte upon the electrodes. The cell includes a cleaning assembly integral with the cell body, and the electrodes of the cell are integrated with a plunger reciprocably mounted within the cell body. In operating position, the electrodes are extended by actuation of the plunger into a thimble insert which, with the components provided by the thimble insert provide the essential components of an operative cell. The plunger, when the cell has become insensitive due to desensitization of the electrolyte, can be withdrawn from the thimble insert, aligned with the cleaning apparatus, the electrodes cleaned and a fresh electrolyte installed upon the electrodes, and the electrodes returned to operative position by mere reactuation of the plunger. The invention also provides a process for maintaining a dry orthophosphoric acid electrolyte in its dry state, as opposed to its metaphosphoric or anhydride states, to increase the period of sensitivity of an electrolytic cell as employed in moisture analyzers, particularly that described herein.

9 Claims, 6 Drawing Sheets

ELECTROLYTIC CELL AND PROCESS FOR THE OPERATION OF ELECTROLYTIC CELLS, FOR MOISTURE ANALYZERS

FIELD OF THE INVENTION

This invention relates to improvements in moisture analyzers. In particular, it relates to trace gas moisture analyzers, and a more effective method for their operation.

BACKGROUND AND PROBLEMS

It is frequently necessary in industrial operations to continuously and accurately measure the moisture concentration of process streams, e.g., hydrocarbon streams, particularly natural gas streams where the moisture is present as a vapor. In The Permutit Company's U.S. Pat. No. 4,589,971 by Donald P. Mayeaux which was issued on May 20, 1986 there is disclosed an instrument, or analyzer for the continuous and accurate measurement, in natural gas streams, of moisture concentrations measured in parts per million (ppm), based on the total volume (or weight) of the gas. The analysis for water vapor is made in the presence of contaminants, e.g., glycols, methanolamine, iron oxide particulates and methanol antifreeze which is often injected into natural gas lines.

Permutit's moisture analyzer, and some earlier moisture analyzers such as that described in U.S. Pat. No. 2,830,945 to F. E. Keidel (over which Permutit's moisture analyzer is an improvement), utilizes a cell which contains a pair of electrodes covered by a hydroscopic electrolyte, which when contacted by a moisture-containing sample will absorb moisture and produce electrolysis, and an electrolytic sensor for detecting as output from the cell an electric current as a function of the amount of moisture contained in the gas passed through the cell. The Permutit cell is characterized as a compartmented structure, a first compartment into which a moisture-containing gas specimen can be admitted, via an inlet, and expelled via an outlet, and a second compartment separated from the first compartment by a semi-permeable membrane through which moisture can be passed. The second compartment contains an electrical circuit which includes at least one pair of electrically isolated electrodes located in close proximity one to another on which can be disposed a hydroscopic substance, or electrolyte, e.g., $P_2O_5$, which is electrically conductive when wet and in contact with both electrodes. A direct current power source of voltage is provided which is sufficient to electrolyze the electrolyte when it is wetted by moisture passed from the specimen or sample through the semi-permeable membrane from the first compartment to said second compartment, as well as current measuring means for measuring the water content of the electrolyte as a function of the current delivered by the power source in electrolyzing the electrolyte. Water molecules dependent upon their concentration within the sampled fluid passing through the first compartment, are transported through the membrane to the electrolyte. The water is disassociated, or electrolytically decomposed to its elemental components, hydrogen and oxygen, by action of the electrical current upon the electrolyte. An electrical signal is produced which is directly proportional to the number of water molecules which are transported through the membrane, and this signal in turn is directly related to the moisture, or water vapor concentration within the sampled gas. Hence, this signal is readily measured and converted electrically to a readout representative of the moisture concentration within the sampled gas. Unlike previous instruments of this type, the dependency upon sample flow rate is eliminated, and replaced by a far more accurate type of physical measurement. Moreover, the separation of the electrolyte from direct contact with the sampled fluid due to the presence of the semi-permeable membrane protects the electrolyte from solids and liquids contamination. It also prevents the electrolyte from being leached, or washed-out by slugs of liquids. The detector response for these reasons remains stable over longer periods of time.

Despite these improvements, the sensitivity of the cell gradually fades with age; albeit at a slower rate than previous cells. Contaminants, particularly those of small molecular size or low molecular weight, e.g., volatile amines, alcohols and the like, pass through the membrane and contact the electrolyte. Moreover, the electrolyte is very gradually dehydrated over a long period of time. For example, the $P_2O_5$ electrolyte is applied as a wet orthophosphoric acid, and water is gradually removed from the electrolyte on application of a sufficiently high voltage as normally applied across the cell. Thus, the orthophosphoric electrolyte in presently used cells over a period of time is gradually reduced to the anhydride $P_2O_5$ form which is less than one-half as active as dry orthophosphoric acid in the electrolytic decomposition of water molecules.

OBJECTS

It is, accordingly, the primary objective of the present invention to provide a novel process, and apparatus, for the analysis of the moisture content of moisture-containing process streams, particularly gaseous process streams, and more particularly moisture-containing gas streams—especially, natural gas streams—over longer periods of instrument sensitivity.

A particular object is to provide a process for maintaining for longer periods of time the sensitivity of moisture analyzers of the type utilizing a cell which contains an electrolyte, particularly $P_2O_5$, in contact with a pair of electrodes such that the moisture of a gaseous sample on contact therewith produces electrolysis, and an electrolyte sensor for detecting as output from the cell an electric current as a function of the amount of moisture contained in the gas passed through the cell.

A further object is to provide an improved trace moisture gas analyzer which can be operated to maintain its sensitivity over longer periods of time, and from which a cell component containing the electrode assembly coated by a previously used electrolyte can be readily removed, the electrode cleaned, the used electrolyte replaced, and the cell unit returned to its operative condition, even by one having little knowledge of the use, and function of the apparatus.

THE INVENTION

These objects and others are achieved by use of the present invention, apparatus and process, embodying improvements in a cell assembly, or operation of a cell assembly, characterized as a compartmental structure which includes (1) a first compartment separated from a second compartment by a partitioning semi-permeable membrane through which moisture can be passed, said first compartment including a fluid or gas inlet into which a sample moisture-containing fluid, especially a gas, can be admitted, and a fluid, or gas outlet through which the sampled fluid, or gas, can be expelled, or discharged, (ii) the second, or adjacent, compartment containing an electrical circuit which includes at least one pair of electrically isolated electrodes located in close proximity one to another upon which can be disposed a hydroscopic substance, or electrolyte, which is electrically conductive when wet and in contact with both electrodes, a direct current power source of voltage sufficient to electrolyze said hydroscopic substance, or electrolyte, when wetted by moisture passed through said semi-permeable membrane from said first compartment to said second compartment, and current measuring means connected in circuit with said direct current power source for measuring the water content of said hydroscopic substance as a function of the current delivered by said power source in electrolyzing said hydroscopic substance, or electrolyte.

The cell of this invention, like that described in U.S. Pat. No. 4,589,971, supra, is thus structured to physically separate, and compartmentalize, (i) the sample gas and (ii) the electrolyte/electrode wire subassembly portion of the cell via the use of a semi-permeable membrane, water molecules from the sample gas passing through the semi-permeable membrane to contact the electrolyte/electrode wire subassembly to produce an electric current which can be measured as a function of the amount of moisture contained in the sample gas. Albeit the physical separation of the sample gas and the electrolyte/electrode wire subassembly provides admirable improvements, the sensitivity of the cell nonetheless declines with continued use due primarily to the inevitable exposure of the electrolyte to contaminants contained within the sample. Thus, membranes are not perfectly selective with regard to water vapor and, albeit many contaminants cannot pass through the semi-permeable membrane to contact the electrolyte, many do; especially some of the lower molecular weight (or small molecule) contaminants, e.g., ammonia, alcohols and volatile amines. Trace quantities of gases which can react chemically with acid electrolytes are frequently present in sample gas streams and, because of this, moisture analyzer cells employing acid electrolytes, such as phosphoric acid and phosphorous pentoxide, are subject to gradual loss of sensitivity when used to analyze such streams. Moreover, reduced sensitivity can result from the gradual dehydration of the orthophosphoric acid. The electrolyte is applied as a wet orthophosphoric acid and depends on catalyzed electrolytic decomposition to remove water. With sufficient voltage it can dehydrate to the anhydride $P_2O_5$ form, which is a very slow process requiring weeks for completion. The $P_2O5$ electrolyte is less than 50% as active as dry orthophosphoric acid in the electrolytic decomposition of water molecules.

The electrolytic cell of this invention is structured so that it can be rapidly cleaned and resensitized by removal of the old electrolyte and replacing it with new electrolyte without the use of tools, or the requirement of special skills. It is structured to physically separate the semi-permeable membrane from the electrolyte/electrode wire portion of the cell, and the latter is structured in the shape of a plunger positioned within a cell body. An inner chamber of the cell is formed by the internal cavity of a thimble insert, and an outer chamber by the space between the thimble insert and a chamber liner. In operative position, the electrolyte/electrode wire assembly, on the forward end of the plunger, is projected into the thimble insert forming a separate sample gas chamber partitioned off from the electrolyte/electrode wire portion of the cell by the separating chamber liner and semi-permeable diaphragm, both a part of the thimble insert. The plunger can be readily retracted from within the thimble insert to a cleaning station and the desensitized electrolyte easily removed, replaced by fresh electrolyte, and the plunger again returned to operative position.

In a preferred method of operating an electrolytic cell of this cell, and indeed any electrolytic cell employing a phosphoric acid electrolyte, voltage is applied across the electrolytic cell in amount sufficient to maintain the electrolyte of the cell in the orthophosphoric form but insufficient to dehydrate the orthophosphoric form to the $P_2O_5$ anhydride or metaphosphoric form of the acid. In general, in accordance with the process of this invention, the voltage applied across the platinum group metal electrode wires of the cell (preferably platinum or rhodium) ranges from about 1.5 volts to about 4 volts, preferably from about 2 volts to about 3 volts; this voltage requirement being sufficient to maintain the electrolyte of the cell in the orthophosphoric form but insufficient to dehydrate the orthophosphoric form to the $P_2O_5$ anhydride or metaphosphoric form of the acid.

The characteristics of a perferred cell assembly, moisture gas analyzer, and combination of cell assembly and moisture gas analyzer, and its principle of operation, will be more fully understood by reference to the following detailed description, and to the attached drawing to which reference is made in the description. The various features and components in the drawing are referred to by numbers, similar features and components being represented in the different views by similar numbers. Subscripts are used in some instances with numbers where there are duplicate features and components, or to designate a sub-feature or component of a larger assembly.

The components of the moisture analyzer are contained within a compartmental housing as described by reference to FIGS. 1, 2, and 8, Column 4, lines 1–68, and Column 5, lines 1–29 of U.S. Pat. No. 4,589,971, supra, these portions of the patent herein referred to being herewith incorporated and made by this reference part and parcel of the present application; the cell assembly 50 referred to and described therein being replaced by the new cell assembly 050 referred to and described in detail hereafter. For convenience, the numbers employed to identify and designate the components of the moisture analyzer of the patent are retained herein for ease of reference, except as relates to the new cell assembly 050. Moreover, the filter assembly depicted by reference to FIGS. 3, 3A and 4, described at Column 5, lines 30–68 and Column 6, lines 1–30 of U.S. Pat. No. 4,589,971 is also useful for clean up of the gas entering the moisture analyzer described herein, and these portions of the patent too are specifically incorporated by reference and made part and parcel of this application. The new cell, and the relationship of the new cell 050 described herein to the moisture analyzer described in the patent will be clear and unequivocal as the following description unfolds.

Figure 8:
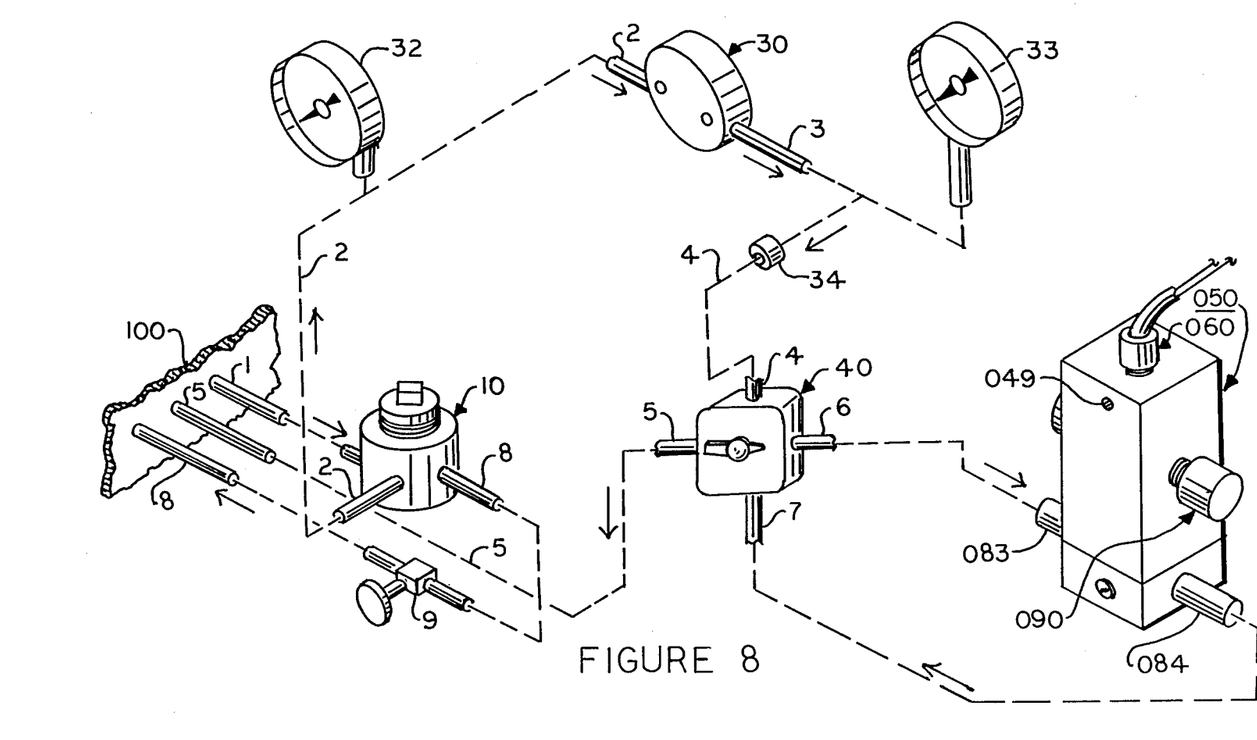
FIG. 8 depicts in exploded fashion, and schematically, the essential apparatus components of a preferred moisture analyzer.

Reference is made first to FIG. 8, for convenience, this figure showing the flow path of the moisture-containing gas on its entry into the moisture gas analyzer, its passage through the new cell assembly 050, and its output from the moisture gas analyzer. The moisture gas analyzer includes a filter 10 with low water adsorption characteristics where solids contaminants are removed from an entering sample gas, the moisture level of which is to be measured. A pressure regulator 30 is employed to reduce the sample pressure to a level desired, e.g., to approximately 5 to 10 pounds per square inch gauge (psig). Gauges 32, 33 located on opposite sides, i.e., upstream and downstream, of the pressure regulator 30, respectively allow the line sample pressure (gauge 32) and analyzer pressure (gauge 33) to be observed. A flow restrictor 34 located downstream of the analyzer pressure gauge 33 maintains a constant flow with a given analyzer pressure (gauge 33), and hence the moisture analyzer is not flow sensitive within a wide range of flow rates. This eliminates any need for using problem prone flow controllers and rotometers. A cell assembly 050, which constitutes the heart of the moisture analyzer, is located downstream of a four-way, or selector valve 40. In one position the selector valve 40 allows sample gas to flow through the filter 10 and pressure regulator 30 circuit while by-passing the cell assembly 050 until these apparatus components are in equilibrium with the sampled gas stream. The sample gas stream leaving the instrument can be viewed to determine if serious amount of solids or liquid contaminants are present, thus avoiding unnecessary cell exposure to major amounts of these contaminants. The isolation of the cell assembly 050 in this manner also protects the cell from the high water levels normally present in ambient air. In introducing a sample gas into the moisture analyzer, the gas with cell 050 cut out of circuit, enters the analyzer via line 1, passes into filter 10 and exits therefrom via line 2, passes through the pressure regulator 30 exiting therefrom via line 3 whereupon it passes through the flow restrictor 34 to enter line 4. The gas then passes through the selector valve 40 and exits therefrom via line 5 whereupon it is vented to the exterior. With the selector switch in alternate position, the moisture-containing sample gas flows into the moisture analyzer and into filter 10, through the regulator 30, flow restrictor 34, selector valve 40 and through the cell assembly 50. The line pressure, or sample pressure is measured by pressure gauge 32 at a point between the filter 10 and pressure regulator 30, and, the analyzer pressure 33 is measured at a point between the flow regulator 30 and flow restrictor 34. The cell assembly 050 can be operated at substantially atmospheric pressure; gas from the cell assembly 050 after passage therethrough being vented to the atmosphere. The analyzer pressure gauge 33 indicates pressure upstream of the flow control restrictor 34, not the cell assembly pressure. Thus, in the alternate switch position (as shown in the figure) the selector valve 40 introduces the cell 050 into the circuit such that sample gas enters the analyzer via line 1, flows through filter 10 to exit therefrom via line 2, enters pressure regulator 30 via line 2 and exits therefrom via line 3, flows through the flow restrictor 34, enters the selector valve 40 via line 4 and exits therefrom via line 6 to flow through cell 050. The sample gas passes out of cell 050 via line 7 and then through selector valve 40 to line 5 whereupon it is vented to the exterior. Aerosol and liquid are discharged from filter 10 via line 8 when the by-pass valve 9 is in open position.

Referring first generally to FIGS. 1–6, the new cell, or cell assembly 050, is generally constituted of a cell body, or tubular housing 051 having an elongate vertical opening 052 in which there is reciprocably mounted a plunger assembly or plunger 060. The elongate vertical opening 052 is axially communicated with a similarly oriented vertical opening 053 of larger diameter within which is mounted a thimble insert 070, which includes an outer cup-like member 071, opening upwardly, and a chamber liner 071 which is contained therein. The chamber liner 072 is also of closed-end tubular design, opens upwardly, and the open end is sized for receipt of the forward end of the plunger 060. The wall of the chamber liner 072 is perforated by circumferentially arrayed openings 073, its lower end is of smaller outside diameter than the diameter of the cup-like member 071 within which it is operatively contained to form an outer annular chamber 074, and a semi-permeable membrane or diaphragm 075 surrounds the perforated wall of the chamber liner 072. The thimble insert 070 is secured in place by a base 080 provided with an inlet 081 for admitting a sample gas into the outer annular chamber 074, and outlet 082 for the removal of sample gas from the annular chamber 074. The forward end of the plunger 060 is provided with externally exposed electrode wires $063_1$, $063_2$, and is of smaller diameter than the inside diameter of chamber liner 072 forming an inner annular chamber 076 when the forward end of the plunger 060 is so positioned. In operation, a small portion of the water molecules contained in the sample gas permeates through the semi-permeable membrane, or diaphragm 075 which covers the outer diameter of the chamber liner 072. The water from the sample gas contacts the electrodes $063_1$, $063_2$ within the inner chamber 076 where it is decomposed to hydrogen and oxygen. The decomposition products are swept out of the cell by sample gas. A cell cleaning assembly 090, constituted generally of a crossbolt 091, or tubular member containing fiberglass wick cartridges $092_1$, $092_2$ alternately disposed on the two sides of the lateral opening 054, are provided for cleaning the electrode wired $063_1$, $063_2$ on withdrawal of the plunger 060, and for application of fresh electrolyte to the cleaned electrode surfaces.

The cell, or cell assembly 050, particular reference being made to FIGS. 1–4, thus includes a cell body, or housing 051 provided by an elongated six-sided block. The two most distant alternately disposed faces of the block, provided by the two far ends of the block, are connected via communicating concentrically aligned axial openings, a bottom opening 053 of relatively large uniform diameter and an upper opening 052 of relatively small uniform diameter, forming in effect a tubular body. The upper terminal end of the small diameter opening 052 is tapped, and provided with threads. A lateral opening 054 of substantially uniform diameter is extended through two alternate faces of the remaining four sides of the housing 051, the center line or axis of this opening intersecting at right angles with the center line or axis of the upper opening 052 through the housing.

The thimble insert 070, which includes the cup-like member 071 and inner chamber liner 072, is contained within the bottom annular opening 053. An upwardly opening cup-like member 071 is thus snugly fitted within the large diameter axial opening 053, located at the bottom of the housing 051. Within the open upper end of the cup-like member 071, which is provided with bottom openings $071_1$, $071_2$, there is fitted a second tubular member 072, the chamber liner, the lower outer side wall of which is of reduced diameter and perforated with a plurality of circumferentially arrayed openings 073. A diaphragm, or semi-permeable membrane 075, suitably constructed of a polymeric material such as unsintered polytetrafluoroethylene, is circumferentially affixed, and retained in place via the encircling wires $075_1$, $075_2$ (FIG. 5), upon the side wall to cover the side openings 073, and the bottom side of the small diameter end of the tubular member 072 is closed. The upwardly faced end of the tubular member 072 is provided with a pair of O-rings $072_1$, $072_2$ for assurance of an air-tight fit between said member and the cell body 051. The cup-like member 071 and inner tubular member 072 which form the chamber liner 070, are retained in place within the large diameter opening 053 by a block 080 mounted upon the base of the housing 051 via a plurality of screws (not shown). The block 080 is provided with an inlet 081 which connects with the opening $081_1$ and outlet 082 which connects with the opening $081_2$ within the cup-like member 071. The inlet 081 and outlet 082, respectively, are provided with fittings 083, 084 to which are connected lines $083_1$, $084_1$, respectively. A sample gas can be introduced via line $083_1$ and opening 081 into the outer annular chamber 074, and removed from the inner annular chamber 076 of the cell 050 after introduction therein.

Figure 1:
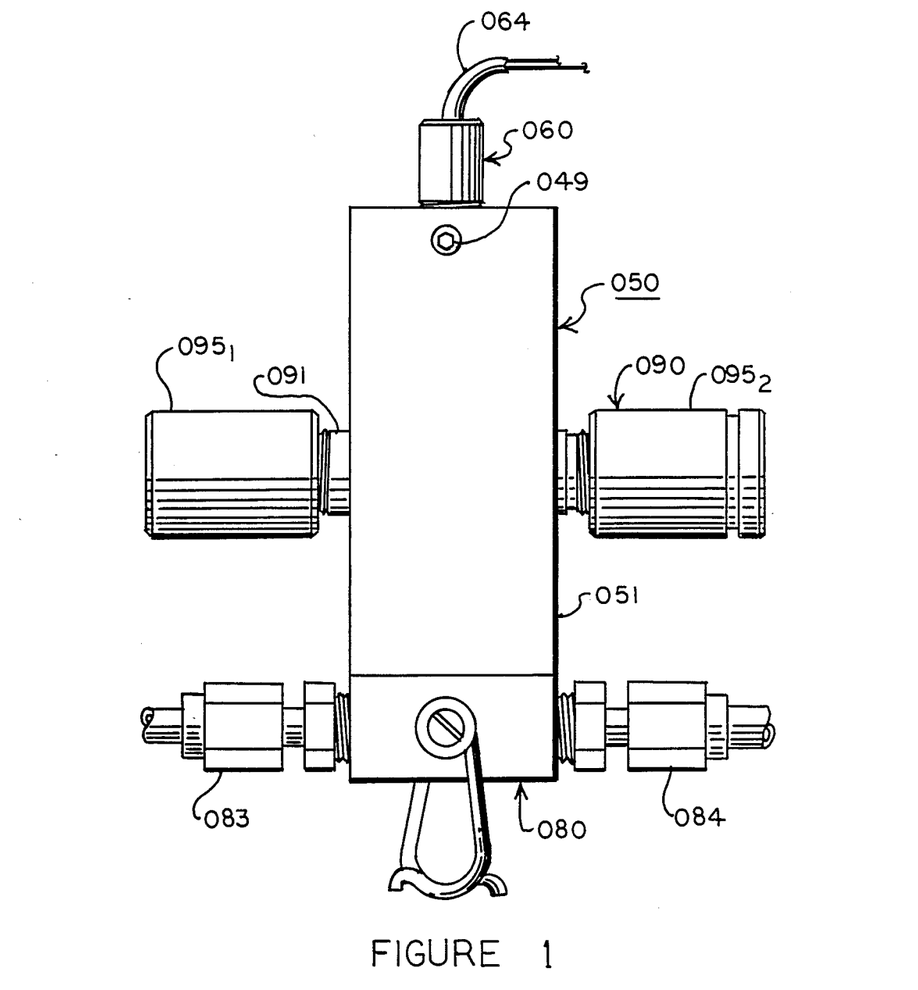
FIG. 1 depicts in side elevation a preferred cell assembly.
Figure 2:
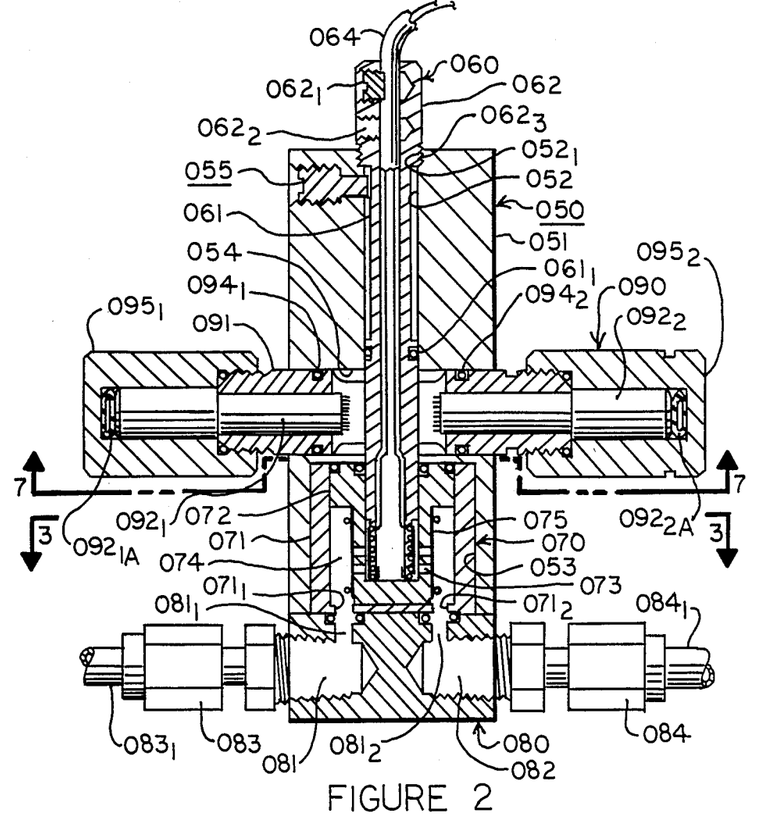
FIG. 2 is a section view showing structural details of the cell assembly of FIG. 1, the cell assembly including generally a cell body, plunger inclusive of an electrode assembly integral therewith reciprocably vertically mounted in said cell body, a thimble insert which includes a cell liner and diaphragm or semi-permeable membrane within a cup-like member which, with the plunger and electrode assembly in place within the thimble insert forms the features of the cell per se, and an electrode cleaning assembly.
Figure 3:
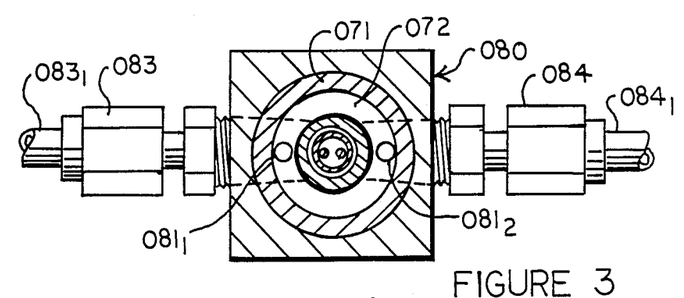
FIG. 3 is a section view of the lower portion or base of the cell assembly, the view being taken across Section 3—3 of FIG. 2.
Figure 4:
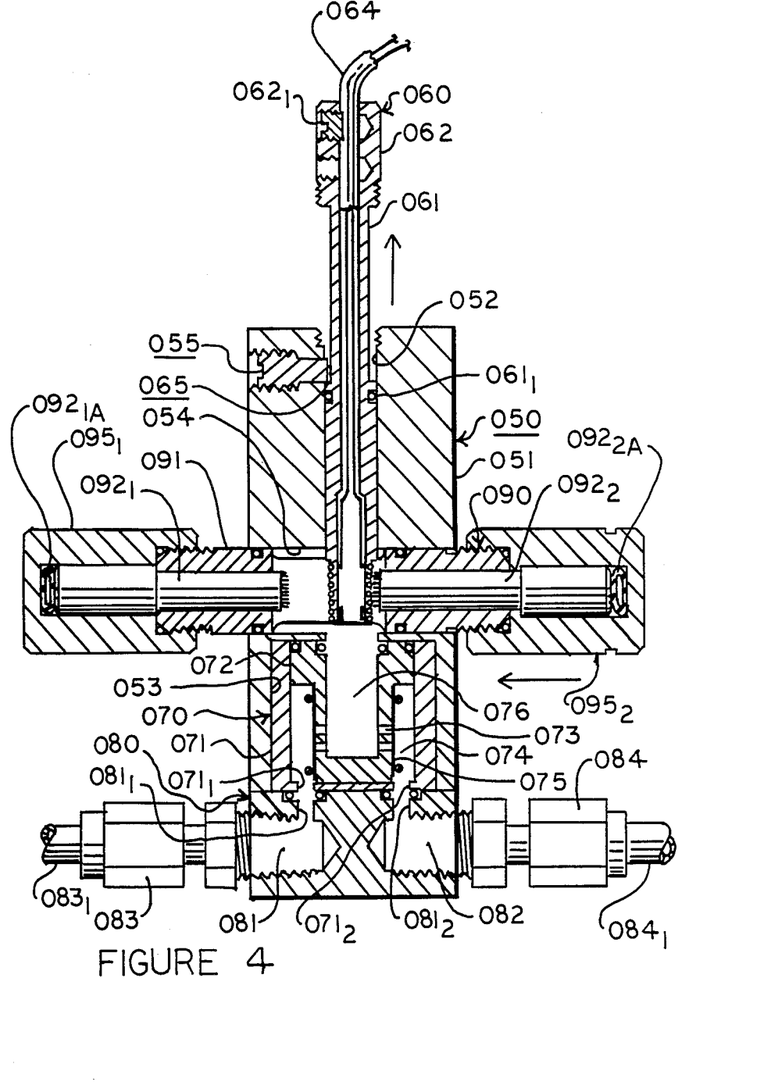
FIG. 4 is a further essentially full section of the cell assembly, this figure taken in conjunction with FIG. 2 and others illustrating the operating function of the electrode cleaning mechanism.

The electrode assembly in the new cell construction is made part and parcel of cell plunger 060, the forward end of which in operative position as shown in FIGS. 1–3, is extended and fitted into the open upwardly faced end of the cup-like member 072. The cell plunger 060 is, in general, constituted of an elongated tubular body 061 upon the rearward or upper upper end of which is provided a tubular knob 062, and upon the forward or lower end of which is provided an exposed pair of wire electrodes $063_1$, $063_2$ of the electrode assembly. The pair of electrode wires $063_1$, $063_2$ are preferably platinum or rhodium. One end of the pair of wires $063_1$, $063_2$ is wound about the forward reduced diameter portion of the plunger 060 (FIGS. 5, 6), is exposed, and lies within the inner annular chamber 076 formed between the external face of the reduced diameter forward end of plunger 060 and the upwardly opening, bottom closed tubular member 072. The non-wraparound portion of the wires $063_1$, $063_2$ are wrapped in an electrically insulating material forming a cable 064 extended upwardly through the interior of the plunger wall 061 and through the tubular knob 062 to the exterior for connection to a voltage supply source. The cable 064 is secured within the knob 062 via the screws, $062_1$, $062_2$ (not shown). The plunger 062, it will be observed, is reciprocably movable within the small diameter opening 052 and the intermediate outer diameter portion of the plunger is fitted snugly therein. The outer portion of the plunger 060 is provided with an O-ring $061_1$, for assurance of an air-tight fit. In its downward position, e.g., as shown by reference to FIG. 2, the exposed wire electrodes $063_1$, $063_2$ are located in their normal position for cell operation, and it will be noted that the plunger 062 is secured in this position by threadable engagement between the external threads $062_3$ of the tubular knob 062 and the interior threads $052_1$ at the upper end of the upper tubular opening 052 of the cell body housing 051. Disengagement between the threads $062_3$ of the knob 062 and the threads $052_2$ of the cell body housing 051 permits limited withdrawal of the plunger 062 to the point that the electrode wires $063_1$, $063_2$ lie within the lateral opening 054 of the housing 051 (FIG. 4). The plunger stop 055, upon which the projecting portion of the plunger 065 impinges on withdrawal of the plunger 062, does not allow withdrawal of the plunger 062 beyond this point, this positioning the exposed portion of the electrode wires $063_1$, $063_2$ within the lateral opening 054 for cleaning and recharging with a fresh electrode.

Figures 5, 6, 7:
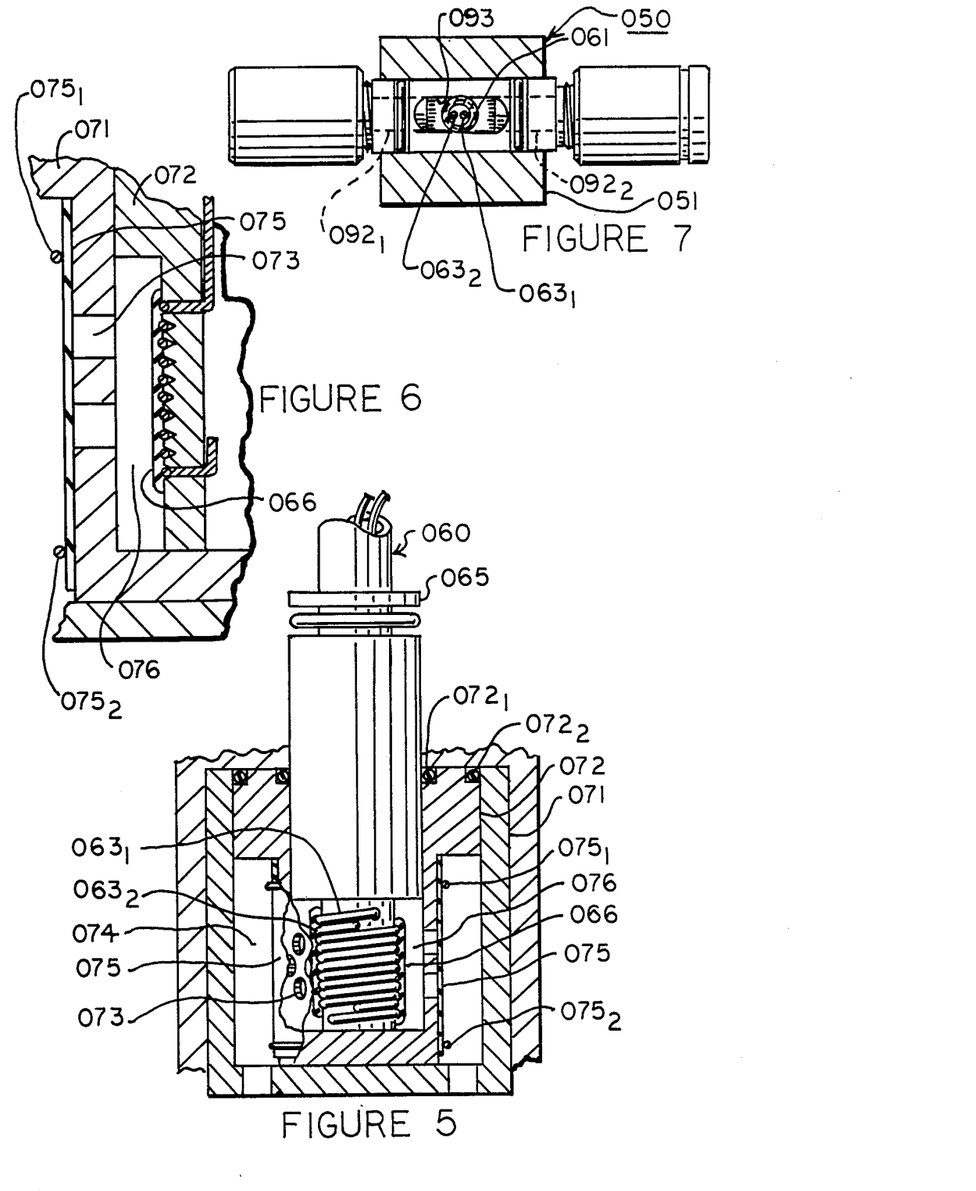
FIG. 5 is an enlarged fragmentary view, in section, of the plunger electrode assembly in its operative functional position within the thimble insert; this view including the details of the surrounding annular chamber, formed by the separating diaphragm or semi-permeable membrane, into which the moisture-containing gas is introduced and withdrawn.
FIG. 6 is an enlarged view in section showing in some detail the manner in which the electrode wires are mounted within the forward end of the plunger, or plunger assembly.
FIG. 7 is a view taken along Section 7—7 of FIG. 2.

In operating position, the plunger 060 is pushed all the way downward, and retained with the exposed ends of the electrode wires $063_1$, $063_2$ lying within the upwardly opening chamber liner, or tubular member 072, as best shown by reference to FIGS. 5 and 6. The knob 062 is threadably engaged with the threads at the upper end of the tubular opening $052_1$ of housing 051. Cell operation, and analysis of a gaseous specimen is performed with the plunger 060 so positioned, this position in effect providing two annular chambers 074, 076 separated by the diaphragm or semi-permeable membrane 075; a first or outer annular chamber 074 into which a moisture-containing sample gas can be introduced via inlet 081 for analysis of its moisture content, and a second annular chamber 076 on the opposite side of the diaphragm or semi-permeable membrane 075 within which lies the exposed pair of wire electrodes $063_1$, $063_2$. Water molecules from a moisture-containing sample gas introduced via inlet 081 into the outer annular chamber 074 will thus permeate through the diaphragm or semi-permeable membrane 075 diffuse and enter into the annular chamber 076 via the circumferentially arrayed openings 073 whereupon the water molecules will come into contact with the electrolyte 066 spread upon the surface of the electrode wires $063_1$, $063_2$ at which the decomposition of water to hydrogen and oxygen takes place. Sample gas will exit the annular chamber 076 via outlet 082.

The cell cleaning assembly 090 is best described by reference to FIGS. 2 and 4. A crossbolt is mounted within the lateral opening 054 of the cell body housing 051, this with the alternately disposed fiberglass wick cartridges $092_1$, $092_2$ mounted therein providing an easy means of cleaning the used electrolyte from the cell and applying a fresh electrolyte. The crossbolt 091 thus includes a tubular member 091 which houses two fiberglass wick cartridges $092_1$, $092_2$, a first dry fiberglass wick cartridge $092_1$ mounted on one side of the opening 052 which is useful for cleaning desensitized electrolyte from the exposed electrode wires $063_1$, $063_2$, and a second fiberglass wick cartridge $092_2$ disposed on the opposite side of the opening 052 which can be wetted with fresh electrolyte for application to the exposed electrode wires $063_1$, $063_2$ after they are cleaned of the desensitized electrolyte. The crossbolt 091 is thus a tubular member through the center of which is cut an elongate slot opening 093, and through the mid portion of which the plunger 060 can be passed when the cell is in assembled condition, reference being made for convenience to FIG. 2. An O-ring $094_2$, $094_2$, respectively, is located on the opposite external faces of the elongate slot opening 093 for sealing purposes, and the oppositely disposed ends of the tubular member 091 are externally threaded and provided with internally threaded open front-end tubular knobs $095_1$, $095_2$. Each fiberglass wick cartridge $092_1$, $092_2$ is constituted of a tubular member, the rearward end of which is closed and the forward end open and packed with a bundle of glass fibers of even length, the front of which is projected outwardly beyond the terminal end of the tube within which it is contained. The second fiberglass wick cartridge $092_2$ is saturated with liquid electrolyte. The electrolyte wets the exposed ends of the fiberglass, and is fed from the cartridge by the wicking action of the fiberglass. Each of the fiberglass wick cartridges $092_1$, $092_2$ are biased such that the glass fibers are projected in the direction of pluger opening 052 via rubber springs $092_{1A}$, $092_{2A}$. When the cell sensitivity drops to an unacceptable level the plunger 060 of the cell can be retracted to the extent limited by the stop 055, this centering the exposed electrode wires $063_1$, $063_2$ within the lateral and crossbolt openings 052, 054, respectively, in alignment with the fiberglass wick cartridges $092_1$, $092_2$. By depressing the crossbolt cleaner knob $095_1$, the dry fiberglass wick cartridge $092_1$ is contacted with the pair of electrode wires $063_1$, $063_2$ which can be readily cleaned and the spent electrolyte absorbed within the fiberglass cleaned via capillary action by rotation of the plunger 060 a few turns in either or both directions. Solids, semi-solids or gum reaction products, resulting from reaction between the electrolyte and contaminants, are readily removed in this manner. The crossbolt 091 is then withdrawn and the electrolyte knob $095_2$ is then depressed to bring the fiberglass ends of fiberglass wick cartridge $092_2$ into contact with the cleaned electrode wires $063_1$, $063_2$. The cell plunger 060 is then rotated a few times in either or both directions, thus action evenly coating fresh electrolyte upon the electrode wires $063_1$, $063_2$. The number of rotations is not critical. Capillary action insures that the number of rotations, or operator skill level does not influence the mount or evenness of the electrolyte coating upon the electrode wires $063_1$, $063_2$. Preferably, a DC voltage is applied to the cell in the cleaning and electrolyte application steps. During cleaning, the bubbling action of the water decomposition reaction, resulting from the cell exposure to the relatively high moisture content inside of the crossbolt area, enhances the capillary removal of spent electrolyte. The high moisture content in the crossbolt is the result of wet electrolyte present in the electrolyte cartridge. Preferably, an electrolyte charge of about 60% phosphoric acid/40% water by weight, is used in the electrolyte cartridge to provide water vapor. This enhances cleaning activity, and more importantly reduces the viscosity of the phosphoric acid to insure even capillary coating of the electrolyte upon electrode wires $063_1$, $063_2$. The resulting bubbling action during electrolyte decomposition also aids in keeping the electrolyte coat at a desired level. Excessive electrolyte tends to decrease the speed of response during a moisture analysis. Too little electrolyte makes cell operation marginal and more susceptible to rapid deterioration when contaminated.

After electrolyte decomposition the crossbolt 091 is re-centered allowing the plunger 060 to be pushed downward into its normal operating position within the thimble insert 070, or inner cell chamber 076.

In general, purging the outer cell chamber with dry gas and applying a DC voltage across the cell electrode wires for approximately 12 hours will dry the electrolyte and prepare the cell for operation. Purging hastens the drying by sweeping out the hydrogen and oxygen resulting from water decomposition. It also sweeps out water molecules which diffuse to the outer chamber. Whereas this procedure can be carried out without purging, the drying will take 30 to 40 hours. The mechanical design of the crossbolt 091 and the plunger 060 prohibits crossbolt movement when the plunger 060 is in its normal, forward operating position with the forward end of the plunger in the inner chamber 076. This insures that the dry wick $092_1$ will not contact the electrode wires $063_1$, $063_2$ and remove electrolyte as the plunger 060 is pushed forward. The design also prevents application of electrolyte in areas other than that of the electrode wires $063_1$, $063_2$. Inadvertent application of electrolyte in non-active portions of the cell or plunger areas would thus absorb water molecules and greatly degrade the cell response time. Furthermore, the assembly of the cell body, the crossbolt 091, and the plunger 060 can be maintained with a single screw 049 (FIG. 1), which also acts as a mechanical stop for the plunger 060.

Figure 9:
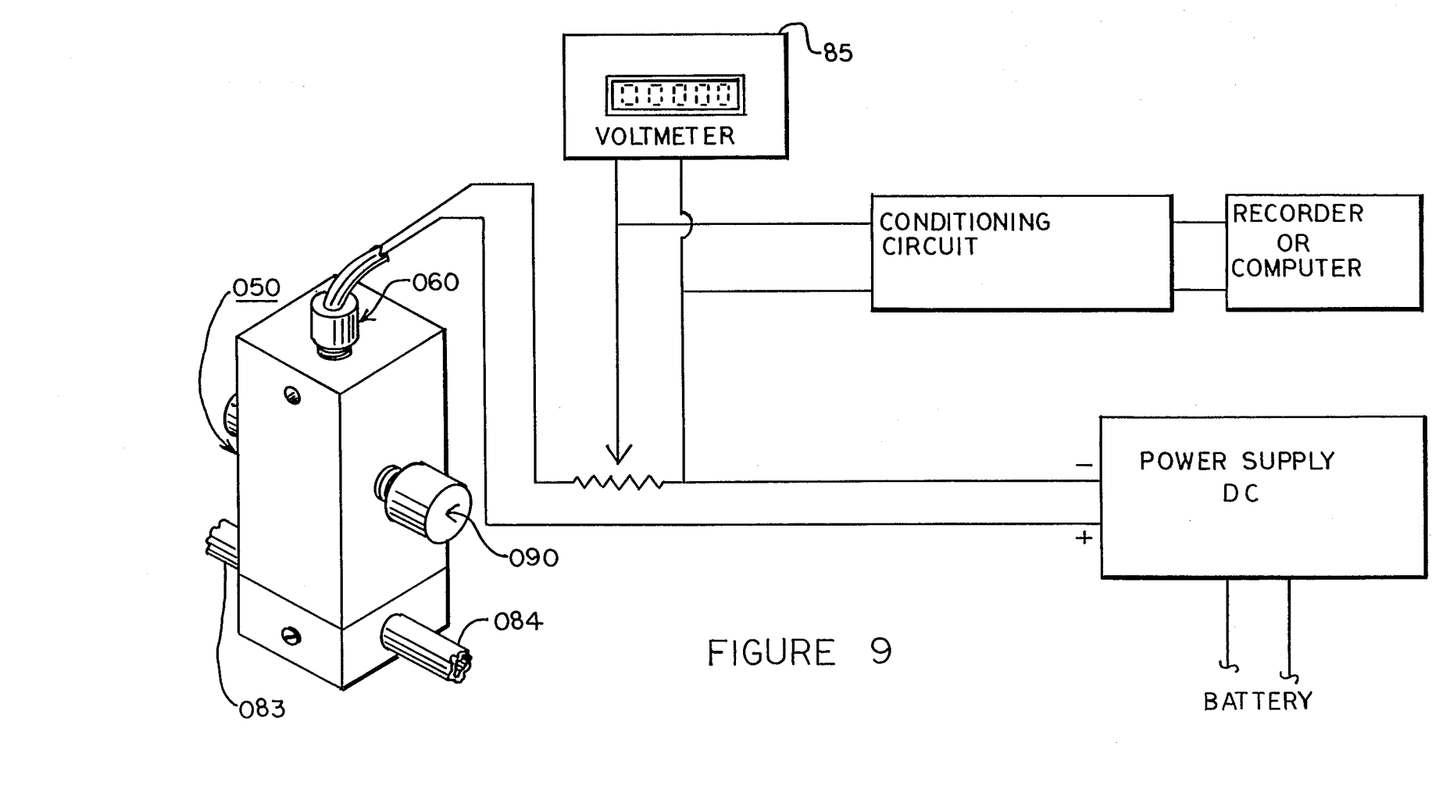
FIG. 9 depicts schematically an electrical wiring diagram of preferred circuitry, readout, and recording components.

An electrical circuit associates with the cell assembly 050 is depicted schematically by reference to FIG. 9. In its more simple form, a voltmeter can be used for measuring and displaying the moisture concentration in the sample gas directly in terms of unit quantity of water per unit quantity of sample gas, this eliminating any necessity for range switching. It also provides a precise means for direct readout of the moisture concentration. Battery power is adequate for such purpose. The voltmeter reads the potential difference that represent the current flow from the cell, this value being representative of the moisture contained within the sample gas. The output from the cell can also be recorded, or sent to a computer, the raw signal from the cell being first sent through a conditioning circuit which buffers the signal, and regulates it in accordance with some desired scale.

Phosphoric acid exists in three states of hydration: orthophosphoric ($H_3PO_4$), the most hydrated state, pyrophosphoric acid ($H_4P_2O_7$), and metaphosphoric acid ($HPO_4$), the least hydrated form of this acid. When wet orthophosphoric acid is electrolyzed in the presence of a platinum group catalyst (e.g., rhodium or platinum wires $063_1$, $063_2$), by a direct current voltage exceeding two volts, the free water will decompose to hydrogen and oxygen. If the voltage is sufficient, e.g., greater than about 3 volts DC, the $H_3PO_4$ will slowly become further dehydrated to the lesser hydrated states of pyrophosphoric acid, metaphosphoric acid, and ultimately to the anhydride phosphorous pentoxide ($P_2O_5$). It has been determined that dry (without free water) orthophosphoric acid is substantially more efficient as an electrolyte, in the electrolytic decomposition of water, than the most hydrated meta and anhydride states $P_2O_5$. It is apparent that the current carrying capacity and/or mobility of ions in the ortho state enhances the water decomposition, and is therefore more important to the overall operation of an electrolytic cell, particularly the electrolytic cell herein defined, than the hydroscopic value of the meta state and $P_2O_5$.

If the applied voltage to a cell is increased beyond 3 volts (in the absence of water) with the electrolyte in the dry ortho state, the conversion to the less hydrated states will be indicated by a rise in the electrical current.

To maintain the electrolyte in its most efficient "dry ortho state" the applied cell voltage must not exceed about 4 volts, and must generally be maintained at about 3 volts, or just below 3 volts. However, when water molecules from sample gas enter the cell in sufficient numbers, the voltage must be increased accordingly, or the cell response will be nonlinear. It is necessary to maintain the optimum voltage for all water concentrations of sample gas to preserve accuracy. Insufficient voltage will yield low cell output, and excessive voltage will cause dehydration of the electrolyte to the meta state, this also resulting in low cell output over a long time period. Even without water molecules entering the cell, the applied cell voltage can be maintained at about 4 volts, preferably at about 3 volts, or just below 3 volts, for an indefinite period of time without formation of the meta state. This appears to be a threshold voltage. With 3 volts applied to the cell, and without water molecules entering the cell, a background current of 17 microamps per square centimeter of cell area is typical. The cell voltage must be increased as the number of water molecules reaching the active cell surface increases. The voltage is increased at the rate of about one volt per 4.8 micrograms of water per square centimeter of cell area per second (1 volt/4.8 mg $H_2O$/sq. cm. cell area/sec). The number of water molecules reaching the cell area is, of course, dependent primarily upon the water concentration of the sample gas and the membrane characteristics. The sample pressure within the cell is generally kept at atmospheric pressure, in which case the membrane has a negligble temperature coefficient. Generally, less the 10% of water molecules entering the outer cell chamber diffuse to the cell into the inner chamber. The cell is designed to decompose water at rates far in excess of even that normally encountered at maximum concentration range. The cell therefore, by design, is not susceptible to diminished sensitivity as electrolyte efficiency is diminished, since the process is essentially membrane limited.

It is apparent that various modifications and changes can be made without departing the spirit and scope of the invention.

Having described the invention, what is claimed is:

1. In an apparatus for detecting and measuring the amount of moisture in a moisture-containing stream which utilizes as part of an electrical circuit an electrolytic cell characterized as a compartmented cell housing formed by an enclosing wall which includes a first compartment separated from a second compartment by a partitioning semi-permeable membrane through which moisture can be passed, said first compartment being contained within the enclosing wall of said cell housing and including an inlet within said wall through which a moisture-containing stream can be admitted, and an outlet through which said moisture-containing stream can be discharged from said first compartment, said second compartment containing at least one pair of exposed wire electrodes which constitute a portion of said electrical circuit and which are adapted to carry a hydroscopic electrolyte which is electrically conductive when wet and in contact with both wires of an electrode pair such that when a moisture-containing stream is admitted via said inlet and discharged via said outlet of said first compartment and contacted with an exposed side of the semi-permeable membrane within said first compartment moisture can be transported from said moisture-containing stream for contact with said hydroscopic electrolyte within said second compartment,
   a direct current power source of voltage sufficient to electrolyze said hydroscopic electrolyte when wetted by moisture passed through said semi-permeable membrane from said first compartment to said second compartment, and
   current measuring means connected in circuit with said direct current power source for measuring the water content of said hydroscopic electrolyte as a function of the current delivered by said power source in electrolyzing said hydroscopic electrolyte,
   the improvement comprising
   a plunger opening within said housing, and
   a plunger carrying the wire electrodes mounted in a reciprocably movable manner within said plunger opening, said electrodes being adapted to be positioned within said second chamber by movement of the plunger for operation of the cell in analyzing a stream for moisture.

2. The apparatus of claim 1 wherein the partitioning semi-permeable membrane which separates said first and second compartments of the cell assembly is a polymeric substance.

3. The apparatus of claim 2 wherein the polymeric substance is unsintered polytetrafluoroethylene.

4. The apparatus of claim 1 wherein the compartmented housing also contains a lateral opening intersecting and in communication with said plunger opening, and cleaning assembly mounted therein which includes disposed on one side of the plunger opening a dry cleaning element and on the other side of the plunger opening a fresh electrolyte applicator, such that the electrode wire carrying portion of the plunger can be withdrawn, desensitized electrolyte can be removed from the electrode wires by said dry cleaning element, fresh electrolyte can be added to the electrode wires by said fresh electrolyte applicator, and the electrode wire carrying portion of the plunger then repositioned within said second chamber for operation of the cell in analyzing a stream for moisture.

5. The apparatus of claim 4 wherein the cleaning assembly is constituted of a crossbolt mounted within the lateral opening, the crossbolt is constituted of a tubular member with a slot opening through which the plunger is projected, a first dry fiberglass wick cartridge useful for cleaning desensitized electrolyte from the exposed electrode wires of the plunger is housed within the tubular member forming said crossbolt on one side of the plunger opening, and a second fresh electrolyte-containing fiberglass wick cartridge is disposed on the opposite side of the plunger opening for applying fresh electrolyte to the electrode wires of the plunger.

6. The apparatus of claim 1 wherein the plunger is of tubular shape, the exposed electrode wires are of small diameter and wrapped about one terminal end of the plunger, the ends of the electrode wires are passed through the plunger wall into a tubular passageway extending through the plunger and connected to an electrical cable which is projected outwardly through the opposite end of the plunger.

7. The apparatus of claim 6 wherein the electrical cable is in electrical contact with a DC power supply source to provide voltage for electrolysis of hydroscopic electrolyte, and current measuring means by virtue of which the moisture content of the sampled stream can be read.

8. The apparatus of claim 1 wherein the bottom portion of the compartmented cell housing is provided with an opening contiguous to and in communication with the plunger opening, a thimble insert is fitted therein above a base provided with an inlet and outlet, said thimble insert including an upwardly opening cup member, the bottom side of which contains an opening therein oriented for communication with said base inlet for the introduction of a moisture-containing stream and an opening oriented for communication with said base outlet for the discharge of said moisture-containing stream, a chamber liner of closed-end tubular design, opening upwardly and sized for receipt of a relatively small diameter portion of the plunger carrying the exposed electrode wires, the bottom side of which is of reduced diameter, perforated by a plurality of openings, covered by said semi-permeable membrane forming in effect outside the perforated wall said first chamber into which the moisture-containing stream is introduced, and discharged, and on the opposite innerside of the perforated wall when said relatively small diameter portion of the plunger carrying the exposed electron wires is introduced therein, said second chamber.

9. The apparatus of claim 8 wherein the base is detachably mounted on the bottom of the cell housing, and retains the thimble insert in place upon the housing.

* * * * *